(12) United States Patent
Schuster et al.

(10) Patent No.: US 7,776,007 B2
(45) Date of Patent: Aug. 17, 2010

(54) DEVICE FOR READYING A NEEDLE FREE INJECTOR FOR DELIVERY

(75) Inventors: Jeffrey A. Schuster, Oakland, CA (US); Paul Stuart Bridges, Menlo Park, CA (US); Graham Gibbins, Hayward, CA (US); Nicola Reid, Hayward, CA (US)

(73) Assignee: Zogenix, Inc., Emeryville, CA (US)

( * ) Notice: Subject to any disclaimer, the term of this patent is extended or adjusted under 35 U.S.C. 154(b) by 716 days.

(21) Appl. No.: 10/596,207

(22) PCT Filed: Dec. 6, 2004

(86) PCT No.: PCT/US2004/040937

§ 371 (c)(1),
(2), (4) Date: Aug. 21, 2007

(87) PCT Pub. No.: WO2005/056077

PCT Pub. Date: Jun. 23, 2005

(65) Prior Publication Data

US 2008/0051700 A1     Feb. 28, 2008

Related U.S. Application Data

(60) Provisional application No. 60/527,514, filed on Dec. 5, 2003.

(51) Int. Cl.
*A61M 5/30* (2006.01)
(52) U.S. Cl. .......................................................... 604/68
(58) Field of Classification Search .................. 604/68, 604/69–72
See application file for complete search history.

(56) References Cited

U.S. PATENT DOCUMENTS

| | | | | |
|---|---|---|---|---|
| 3,625,208 | A * | 12/1971 | Frost et al. | 604/68 |
| 3,782,380 | A * | 1/1974 | Van Der Gaast | 604/68 |
| 4,941,880 | A * | 7/1990 | Burns | 604/143 |
| 5,499,972 | A * | 3/1996 | Parsons | 604/68 |
| 5,514,097 | A * | 5/1996 | Knauer | 604/136 |
| 5,865,795 | A | 2/1999 | Schiff et al. | |
| 5,879,327 | A * | 3/1999 | DeFarges et al. | 604/68 |
| 5,891,086 | A * | 4/1999 | Weston | 604/70 |
| 6,558,348 | B2 * | 5/2003 | Parsons | 604/68 |
| 6,585,685 | B2 * | 7/2003 | Staylor et al. | 604/68 |
| 6,613,010 | B2 * | 9/2003 | Castellano | 604/68 |
| 6,641,554 | B2 * | 11/2003 | Landau | 604/68 |
| 6,669,664 | B2 | 12/2003 | Slate et al. | |

(Continued)

FOREIGN PATENT DOCUMENTS

WO    WO 91/12839    *   9/1991

*Primary Examiner*—Nicholas D Lucchesi
*Assistant Examiner*—Victoria P Campbell
(74) *Attorney, Agent, or Firm*—Karl Bozicevic; Bozicevic, Field & Francis LLP

(57) ABSTRACT

A needle-free injector device comprising a latch having a safe position which disables the triggering of the device, and a ready position which restrains movement of a dispensing member but enables triggering and a triggered position which permits movement of the dispensing member is disclosed. An additional safety mechanism blocks the triggering of the device until removed. A cap is provided to maintain the sterility and stability of the drug formulation and is configured such that the cap removal is required prior to placing the device in a ready to trigger state.

8 Claims, 9 Drawing Sheets

U.S. PATENT DOCUMENTS

| | | | |
|---|---|---|---|
| 6,755,220 B2 * | 6/2004 | Castellano et al. | 141/27 |
| 6,824,526 B2 * | 11/2004 | Castellano | 604/68 |
| 6,939,319 B1 * | 9/2005 | Anstead et al. | 604/68 |
| 6,979,310 B2 * | 12/2005 | Navelier et al. | 604/70 |
| 7,018,356 B2 * | 3/2006 | Wise et al. | 604/68 |
| 2001/0031945 A1 * | 10/2001 | Haar et al. | 604/68 |
| 2002/0099329 A1 * | 7/2002 | Castellano | 604/70 |
| 2002/0123718 A1 * | 9/2002 | Landau | 604/70 |
| 2002/0151840 A1 * | 10/2002 | Castellano | 604/68 |
| 2002/0161334 A1 * | 10/2002 | Castellano et al. | 604/187 |
| 2002/0188251 A1 * | 12/2002 | Staylor et al. | 604/70 |
| 2003/0078535 A1 * | 4/2003 | Castellano | 604/70 |
| 2003/0083612 A1 * | 5/2003 | Castellano | 604/70 |
| 2003/0093030 A1 * | 5/2003 | Landau | 604/70 |
| 2003/0199814 A1 * | 10/2003 | Parsons et al. | 604/68 |
| 2004/0015126 A1 * | 1/2004 | Zierenberg et al. | 604/72 |
| 2004/0087896 A1 * | 5/2004 | Wise et al. | 604/68 |
| 2004/0127846 A1 * | 7/2004 | Dunn et al. | 604/82 |

* cited by examiner

DEVICE FOR READYING A NEEDLE FREE INJECTOR FOR DELIVERY

BACKGROUND OF THE INVENTION

Needle-free injectors are used as an alternative to needle-type hypodermic injectors for delivering liquid drugs and other substances through the skin and into the underlying tissue. The drug is dispensed by a piston from a drug capsule at pressures high enough to pierce the skin. Typically, the drug capsule will comprise a hollow cylindrical chamber narrowing to a discharge orifice at one end, with the piston slidingly and sealingly located at the other. The piston is driven towards the orifice to dispense the drug by a dispensing member. Typically devices are powered by a variety of means, such as a spring (the spring force being supplied by a resilient element or a pressurised gas) or pyrotechnic charge. Examples of such devices are described in U.S. Pat. Nos. 5,891,086 and 5,480,381

For spring powered needle-free injectors, the spring constantly exerts a force on the dispensing member prior to use and a restraining means is required to prevent the dispensing member from moving under the force of the spring. The needle-free injector is triggered by moving the injector into a condition in which the restraining means no longer has a restraining effect, thus permitting the dispensing member to move.

It is often desirable for the triggering of the delivery of the medication to involve a very modest force, for example by the patient pressing a button or pressing the injector against the injection site. However, this low force can cause premature triggering, such as when the device is dropped, or when the cap over the injection orifice that maintains formulation stability and sterility on storage is removed.

A problem exists during the assembly of such devices—producing a device which is easy to operate, may result in a device which is also easy to accidentally trigger during manufacture and assembly. This is both wasteful and can be a safety hazard to the personnel involved.

WO 97/37705 addressed this issue by providing a device for dispensing a material or article, which comprises a spring, which provides an energy store, a dispensing member movable to effect dispensing under the force of the spring, latch means having a first position which prevents triggering of the device, a second position in which it restrains movement of the dispensing member but enables triggering, and a third position in which it permits such movement, trigger means operable by the user for moving the latch means from said second position to said third position, the first position being a safety mechanism effective before the device has been completely assembled to prevent movement of the latch means to the third position For the embodiments of the inventions disclosed in WO 97/37705, the safety mechanism is disengaged at the end of the assembly process, using a tool inserted into the device to move the latch from the first position to the second position. with the latch being restrained from moving to the third position by an outer-ring. The triggering means, which functions by moving the latch so that it is no longer restrained by the outer-ring, is then restricted from operating by a tear-off band, which physically stops the movement of the latch with respect to the outer ring, the band being removed prior to triggering the device.

As an alternative to the above, it may be advantageous to store the devices in the first position, with the original safety mechanism engaged. The devices are stored for up to three years before use and from both a general safety and device performance perspective there are advantages to keeping the safety mechanism engaged. Then following storage, just prior to triggering, an attachment to the device is used to disengage the safety mechanism.

In addition, the orifice must be kept sealed during storage to ensure stability and sterility of the drug product. The removal of the orifice seal is preferably combined with the disengagement of the safety mechanism, to ensure the system is easy to use, and to ensure that the orifice seal is removed prior to the disengagement of the safety mechanism, so that it is not possible that the act of removing the orifice seal triggers the delivery of the drug.

SUMMARY OF THE INVENTION

According to the present invention, there is provided a device for readying a needle free injector for delivery. The injector comprises a energy store, such as a pyrotechnic charge, a mechanical spring, or preferably a pressurized gas spring, and a dispensing member movable, to effect dispensing, under the force of the spring. The invention provides a cap comprising a seal covering the injection orifice to ensure stability and sterility of the contents, and a mechanism for removing said cap. The invention also provides a mechanism for changing the state of the device from a safe state to a ready to deliver state. The safe state is characterized by an inability to accidentally deliver the contents, when for example, the device is dropped, the cap is removed, or the device is otherwise affected. The invention also provides for a linkage between the two mechanisms, such that they must be completed in the correct order, ie the cap is removed while the device is in the safe state.

It is preferred that the act of removing the cap and placing the device in the ready to deliver state be accomplished in a single motion, for example by (but not limited to) having a lever, the end of which is attached to the cap, and the base of the lever actuating the safety mechanism. However, it could also be accomplished in two motions, for example wherein the removal of the cap exposes a safety mechanism which is subsequently activated by the user, or alternatively wherein the cap is removed, exposing the end of the lever to allow the lever to be pivoted, placing the device in the ready to deliver state.

In one embodiment, the removal of the cap and the placing of the device into the ready state exposes a button, said button being pushed by the user to deliver the contents. However, it is preferred that the act of pressing the delivery orifice against the delivery site is what triggers the device to deliver.

An advantage of the invention is that the cap keeps the contents sterile until the delivery It is another advantage of the invention that the cap maintains the stability of the contents, especially to evaporation.

It is another advantage that the device keeps the injector in the safe state until it is ready to deliver.

It is another advantage that the device ensures that the injector is in the safe state until after the cap is removed, to ensure that the act of removing the cap does not lead to accidental delivery, by for example, accidentally pressing on a trigger button or accidentally pressing the end of the injector in a way that mimics pressing the injector into the skin, causing premature delivery.

These and other advantages will be readily apparent to those skilled in the art.

In the preferred embodiment, the invention provides a latch means having a first position wherein the device is safe, and cannot trigger until the latch is forcibly moved. The latch also has a second position, which it restrains movement of the dispensing member, a third position which releases the device to cause delivery, and a trigger means operable by the user for causing the latch means to move from said second position to said third position. Moreover, there is provided a second safety mechanism which engages and disables the trigger until after the cap has been removed and as the device is placed into the ready to trigger state. The invention is linked such that it cannot be activated to move the latch from the first to the second position or disengage the second safety mechanism until the cap providing a sterile barrier to the formulation within drug capsule has been removed.

These and other objects, advantages, and features of the invention will become apparent to those persons skilled in the art upon reading the details of the embodiments as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

A number of different embodiments of the invention are described in the following section making reference to the accompanying drawings, in which.

DETAILED DESCRIPTION OF THE INVENTION

Before the present device and method are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. AR publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a storage means" includes a plurality of such storage means and reference to "the spring" includes reference to one or more springs and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1:
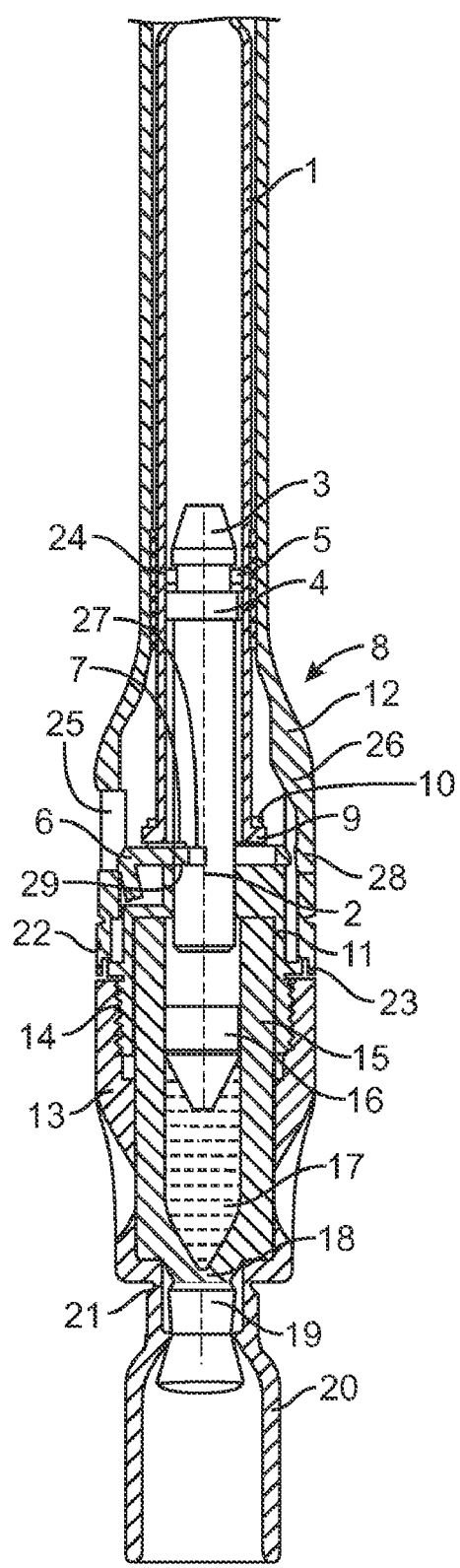
FIG. 1 presents a longitudinal cross-section through the preferred embodiment of the invention.

The embodiments of the invention disclosed are based on Aradigm's (formerly Weston Medical's) Intraject needle-free injector, described in WO 95/03844. FIG. 1 presents a longitudinal section through the Intraject needle-free injector prior to integration with the device of the present invention. In FIG. 1, the injection force is provided by a compressed gas spring, which comprises a cylinder 1 enclosed at one end containing a gas, typically nitrogen, typically at a pressure between 150 and 300 bar. Contained within the cylinder is a dispensing member 2. The end of the dispensing member has a frusto-conical, truncated cone—portion 3 and a flange 4. There is a double o-ring seal 5 situated between the truncated cone section 3 and the flange 4. Prior to triggering the device, the dispensing member 2 is held in the position illustrated in FIG. 1 by a latch 6 which sits in a groove in the dispensing member. The upper surface of the groove forms a cam surface 7. Consequently, there is force urging the latch to move to the left. In the configuration shown in FIG. 1, the latch is restricted from moving by the outer ring 8.

At the lower end of the cylinder 1, there is an outwardly directed flange 9. The cylinder is held in place by crimping the flange 9 to another outwardly directed flange 10 on the upper end on a coupling 11. The sleeve 8 consists of an upper sleeve portion 12 within which the cylinder is situated, and a lower sleeve portion 13. The lower sleeve portion 13 is connected to the coupling 11 by inter-engaging screw threads 14 formed on the inner and outer walls of the lower sleeve portion 13 and the coupling respectively 11.

The injector has a cartridge 15 which contains the medicament. In the cartridge there is a piston 16, slidingly and sealingly located therein. The piston 16 may comprise a cylindrical portion containing two larger diameter ribs, and a frusto-conical portion. The piston 16 is in contact with the medicament 17 and at the other end of the cartridge 15 there is a discharge orifice 18. Adjacent to the orifice 18 there is an interface seal 19 contained within a seal carrier 20. The interface seal 19 is required for filling the needle-free device as described in PCT/GB9700889. A stopper 20a seals the medicament into the capsule. Seal 19, seal carrier 20, and stopper 20a, comprise the cap that must be removed prior to delivery.

To place the device in the ready to deliver state, the cap must be snapped off at the frangible joint 21. This removes the seal 19 and exposes the orifice 18. The trigger blocking mechanism 22, which prevents the medication cartridge from moving back toward the upper sleeve portion 22, thereby preventing delivery, is removed. Finally, latch 6 must be moved from the first (safe) position, to the second (ready to deliver) position, The latch 6 is incorporated into a groove in the dispensing member 2—not only does the groove have a cam surface 7 but also a locking surface 27 which is perpendicular to the dispensing member axis and is located radially inward of the cam surface 7. Additionally, to access the latch 6 there is an opening 28 in the upper sleeve 12, which prior to triggering is aligned with the latch 6.

Figure 2A:
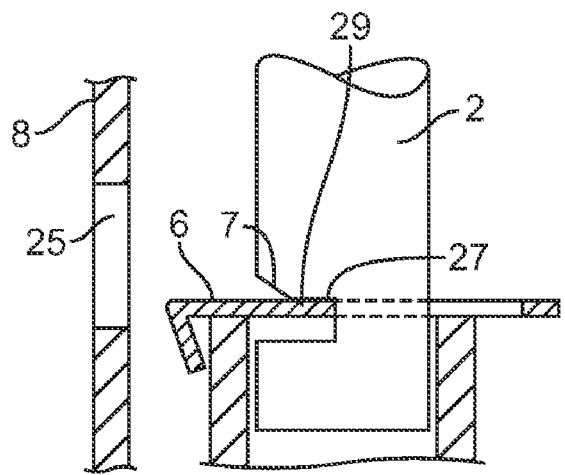
FIGS. 2a, b and c show the latch 6 and dispensing member 2 part of the injector from FIG. 1 in the three stages ending in triggering. In (a) the latch 6 is in the first, or safe position. In (b) the latch 6 is in the second position, the non-safety, ready to trigger position. In (c), the latch 6 is in the third position, following triggering.

FIGS. 2a, b and c illustrate the operation of the safety mechanism. When the latch and dispensing member are initially assembled, the latch occupies the first (safe) position, as shown in FIG. 2a. In this position, the dispensing member-engaging latch portion 29 is acted on by the locking surface 27. Frictional force ensures that the latch is held rigid by the locking surface—typically the dispensing member exerts a force of at least 100N.

Figure 2B:
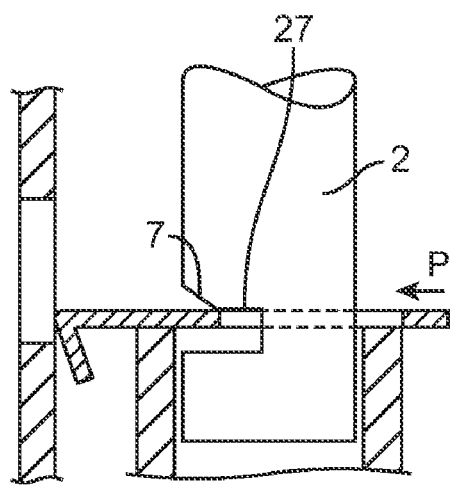

The latch is placed in the second (ready to deliver) position using a pin which fits through opening 28 to push the latch in the direction of the arrow P into the position shown in FIG. 2b, (and in FIG. 1). In this position the dispensing member engaging latch portion 29 is in contact with the radially inner end of the cam surface 7.

Figure 2C:
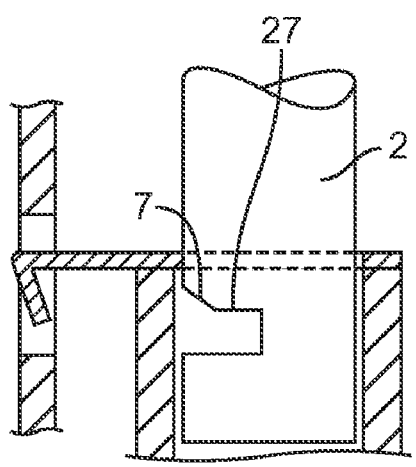

To cause delivery, the orifice 18 is then placed against the skin of the patient. Practically, this involves holding the device by the upper sleeve 12 portion. The upper sleeve 12 is then moved downwards with respect to the lower sleeve 13, bringing aperture 25 in the wall of the upper sleeve portion 8 into alignment with the latch 6. The latch then moves to the left into the aperture 25, under the force exerted on it by the cam surface 7 formed in the dispensing member 3 into the position shown in FIG. 2c. The injector then delivers.

Figure 3:
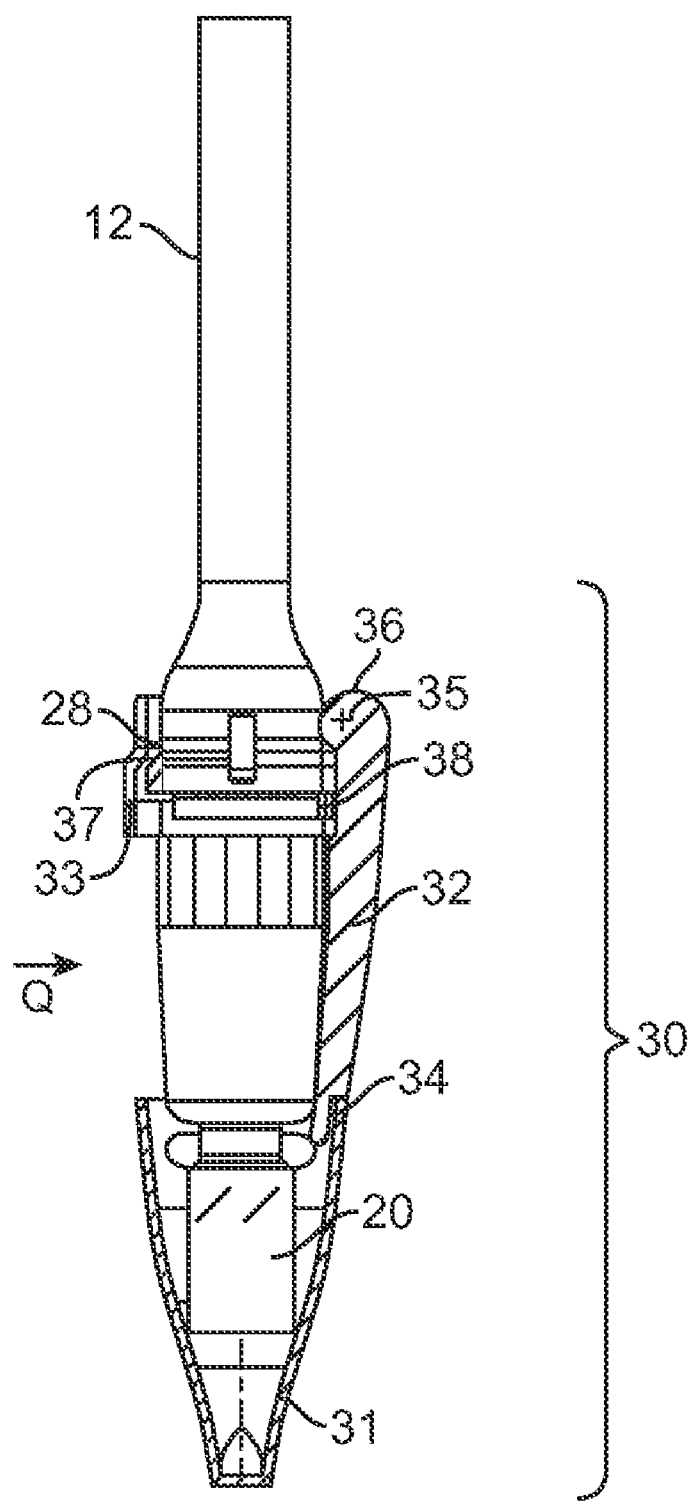
FIG. 3 illustrates a needle free injector with one embodiment of the attachment for disengaging the safety mechanism.
Figure 4A:
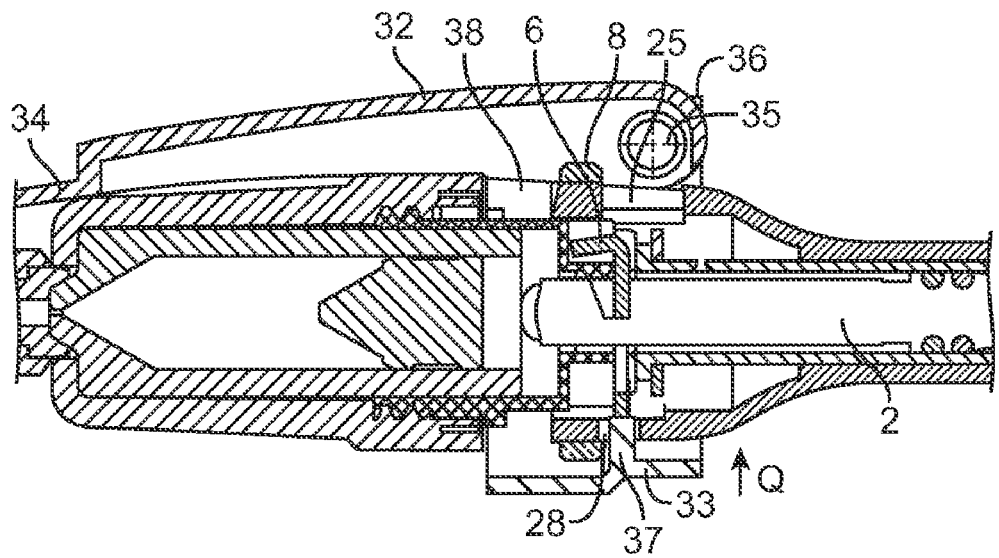
FIGS. 4a and b show the latch 6, dispensing member 2 and collar 33 components of FIG. 3 with the latch 6 in the first, safe position (a) and the second, ready to trigger position (b) respectively.

It is advantageous to have a mechanism that places the device in the ready to deliver state in a simple motion or motions. FIG. 3 illustrates one embodiment of the combined needle-free injector plus means for disengaging the safety mechanism 30. In this Figure, the means for disengaging the safety mechanism consists of a cap 31 enclosing, and holding rigidly, the seal carrier 20, a lever 32 and a collar 33. The lever 32 and collar 33 are presented in more detail in FIGS. 4a and 4b. The lever contains a lip 34 at the far end, over which the cap 31 is positioned. This ensures that the lever 32 cannot be moved before the outer cap 31 is removed, which in turn ensures that the user cannot move the latch or disengage the safety mechanism until the cap has been removed. The lever 32 is pivoted around the pivot axis 35, with the pivoted surface in contact with injector being a cam surface 36. The force required to pivot lever 32 is in the range from about 2N to about 30N. The collar 33 contains a pin 37 which extends into the device through the opening 28 in the upper sleeve 12 to impinge on the far side of the latch 6, see FIG. 4a. The force required to move the latch is in the range from about 20N to about 120N. To stop the upper sleeve section 12 moving with respect to the lower sleeve section 13, there are block sections 38 between the upper and lower sleeves, which form part of the collar 33. The relative position of the block sections 38 with respect to the lever 32 is more clearly presented in the end—on view of the device shown in FIG. 5a.

Figure 4B:
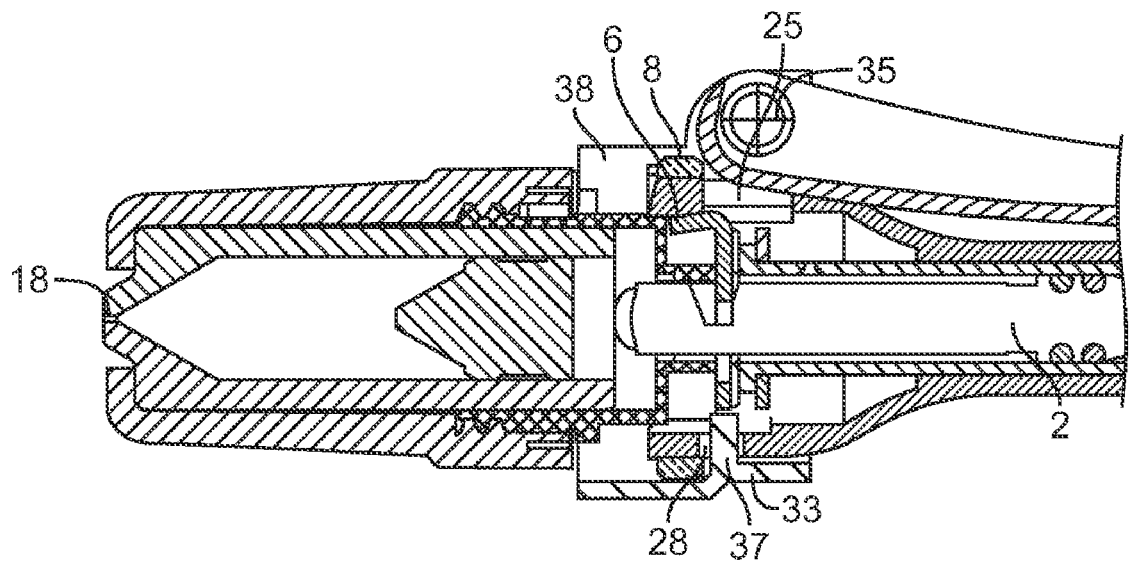
Figures 5A, 5B:
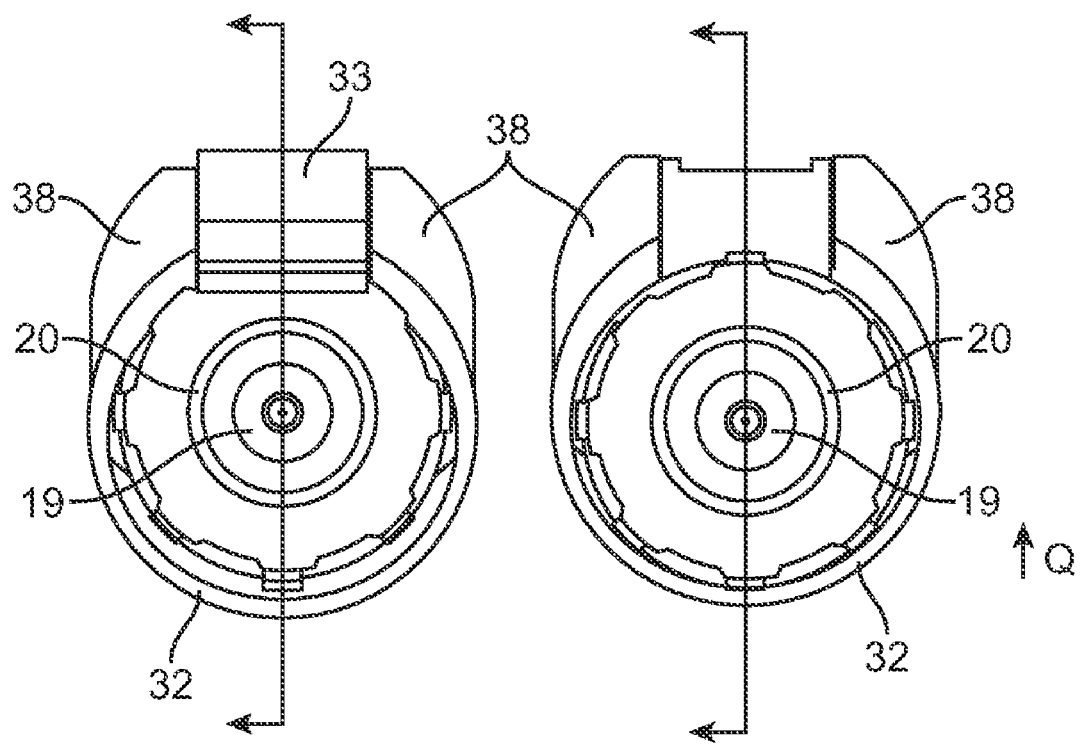
FIGS. 5a and b present end on views of the device in FIG. 3 showing a second safety mechanism comprising block sections, with the (a) the block sections 38 engaged and (b) the block sections 38 disengaged.

To deliver the device contents, the cap 31 is removed, exposing the injection orifice 18. With the outer cap 31 removed, the lip 34 is exposed, enabling the lever 32 to rotate about the pivot axis 35. Only when the outer cap 31 is removed can the lever 32 be rotated. As the lever 32 rotates, the cam surface 36 forces the collar 33 to move in the direction Q in FIGS. 3, 4a and 5b pushing the pin 37 against the latch 6. When the lever 32 has rotated through a complete cycle, approximately 180° as shown in FIG. 4b, the latch 6 moves to the second position, as shown in FIG. 2b. The blocks 38 no longer restrict the movement of the upper sleeve 12 with respect to the lower sleeve 13 and the device can trigger as described above. The relative movement of the block 38 with respect to the sleeve section 12 and 13 is seen in the end on view presented in FIG. 5b. By integrating the cap 31 to the lever 32 with a flexible joint at the tip 34, the mechanism can also be configured to ensure that the user removes the stopper and sets the safety in a single action.

Figure 9:
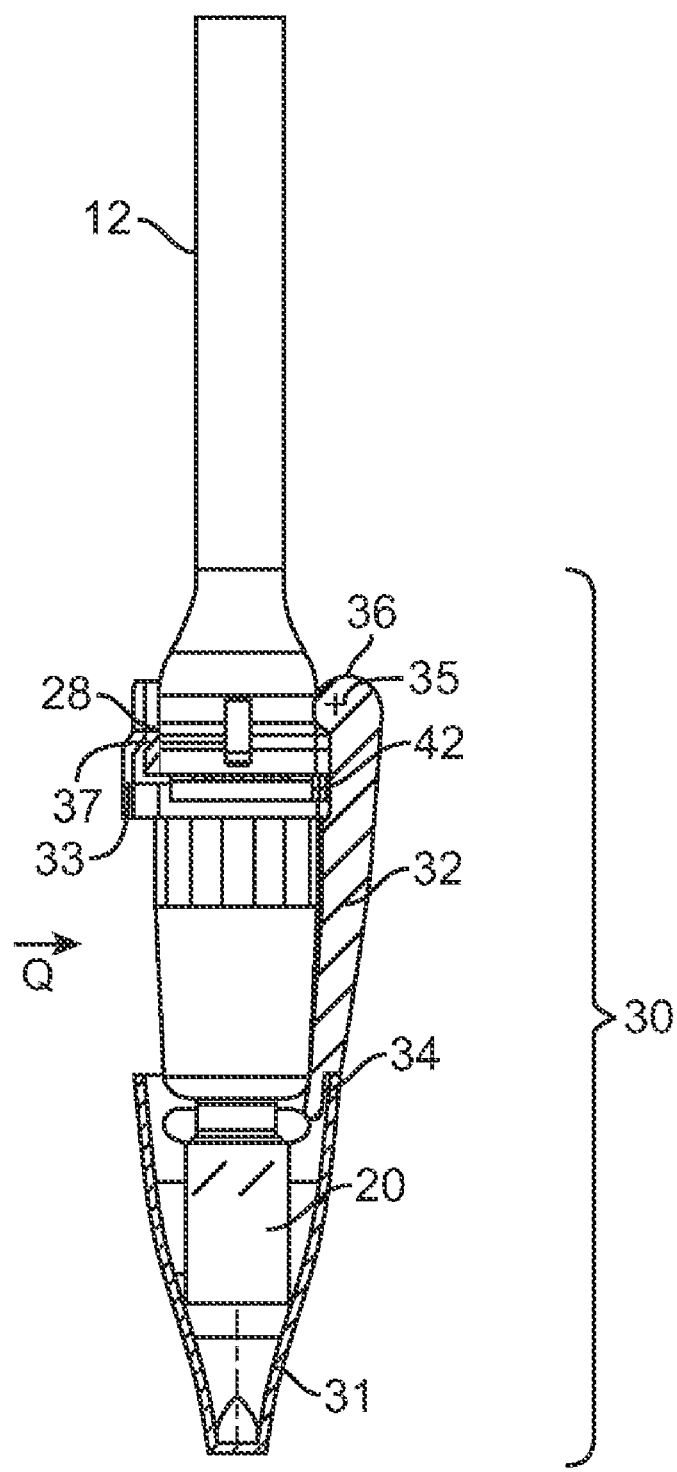
FIG. 9 shows the needle-free injector as shown within FIG. 3 but with the button firing mechanism.

FIG. 9 shows an alternate embodiment from FIG. 3 wherein rather than using the blocks 38, the movement of the lever 32 exposes a trigger button 42, the trigger button 42 subsequently being pressed by the subject to delivery the medication.

Figure 6A:
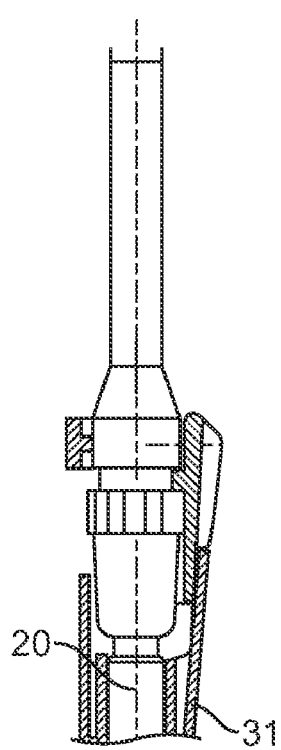
FIGS. 6a, b and c illustrate another embodiment of the attachment for disengaging the safety mechanism (a) with the outer cap 31 in place, (b) with the outer cap 31 inverted to cover the seal carrier 20 and (c) with the seal carrier 20 snapped off by applying pressure to the outer cap 31.
Figure 6B:
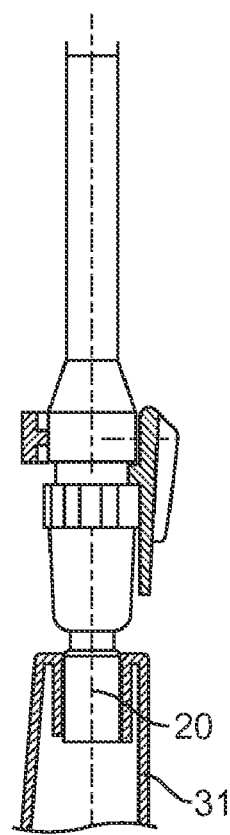
Figure 6C:
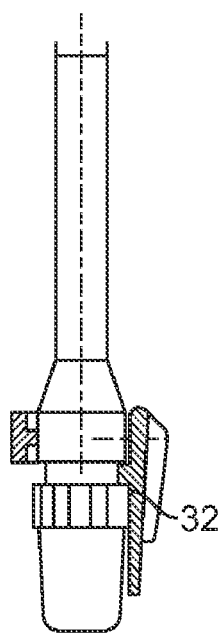

Another embodiment of the invention is shown in FIGS. 6a, b and c. In FIG. 6a the as-received device is presented. To operate the device the outer cap 31 is removed, leaving the seal carrier 20 intact. The outer cap 31 is then inverted and placed back over the seal carrier 20, as shown in FIG. 6b. Pressure is then applied to the outer cap 31 to break the frangible seal between the seal carrier and the lower sleeve, as shown in FIG. 6c. The device is then placed in the ready to deliver state by rotating the lever 32 as described above and presented in FIGS. 4a and b.

Figure 7A:
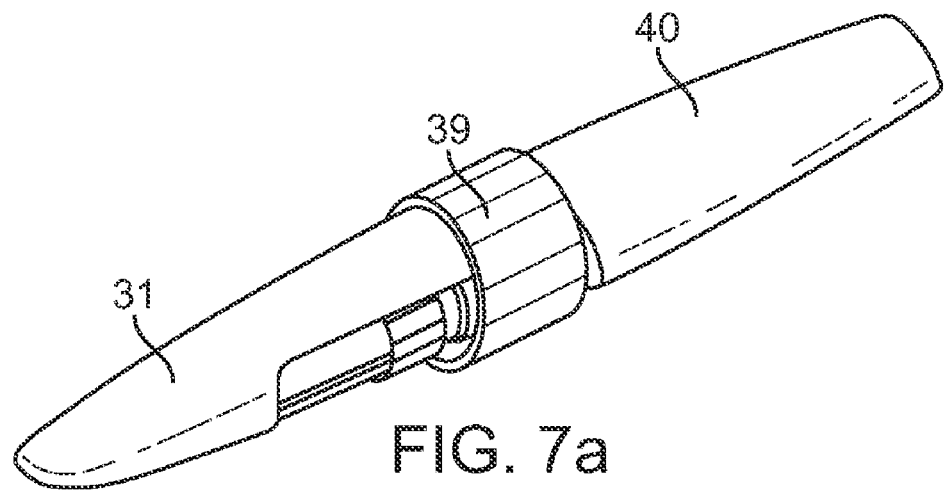
FIGS. 7a, b, c present the third embodiment of the attachment for disengaging the safety mechanism (a) with the outer cap 31 in place, (b) with the outer cap 31 removed, removing the seal carrier 20 and (c) on rotating the ring section 39.
Figure 7B:
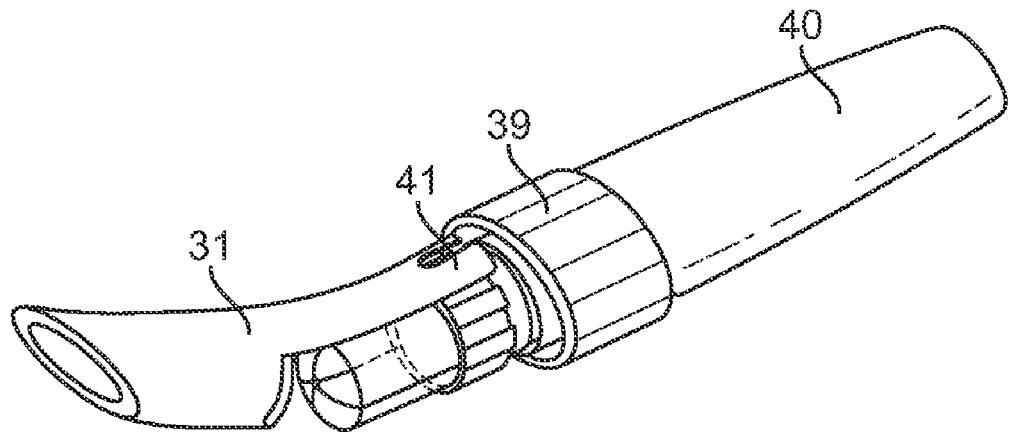
Figure 7C:
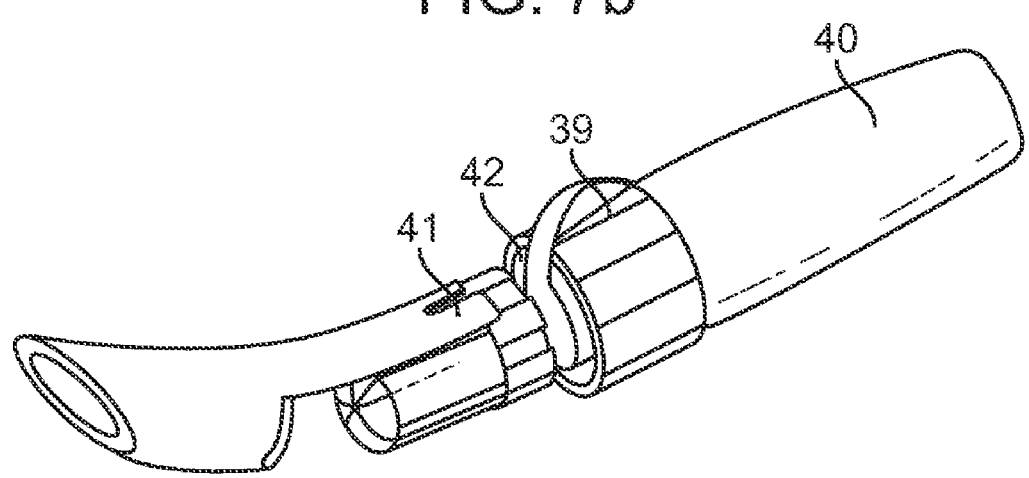
Figure 8A:
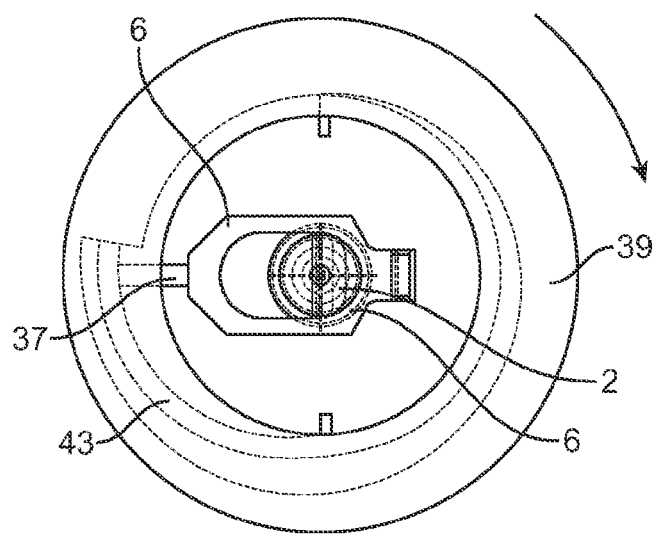
FIGS. 8a and b present a cross-sectional view of the injector in FIG. 7 showing a) the safe position and (b) the ready to trigger position.
Figure 8B:
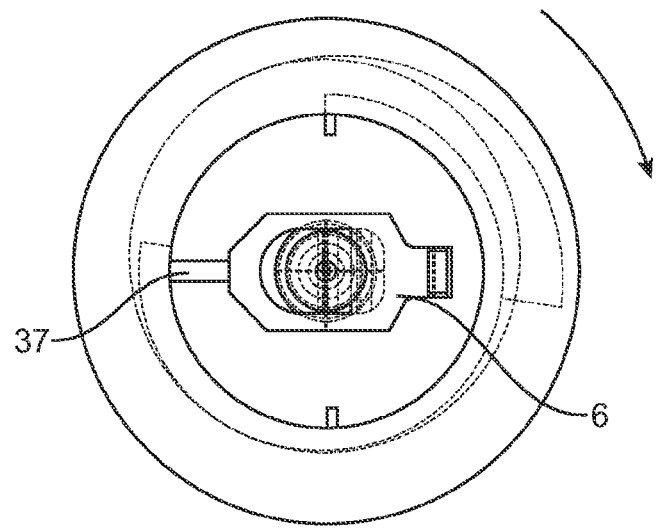

A third embodiment of the invention is shown in FIGS. 7a, b and c. This version of the attachment for disengaging the safety mechanism consists of an outer cap 31 covering and holding rigid the seal carrier 20—not shown in FIG. 7a—, a collar section 39 and a barrel section 40. The needle-free device fits within the barrel section 40 upper sleeve portion 12 first, so that the longitudinal axis of the device is aligned with the longitudinal axis of the barrel section 40. The needle-free device is held rigidly within the barrel section 40. The collar section 39 fits over and is attached to the barrel 40, so that the collar section 39 is free to rotate about the axis of the device in a clockwise direction when the outer cap 31 has been removed. The outer cap 31 contains a locking mechanism 41 which locks the collar 39 rigid when the cap 31 is in place. To trigger the device the outer cap 31 is removed, which in turn removes the seal carrier 20, exposing the injection orifice 8. The collar section 39 is now free to rotate clockwise about the axis of the needle free device. Because the cap 31 is locked into the collar section 39, this ensures that the user cannot move the latch or disengage the safety mechanism until the cap has been removed so forcing the user to prepare the device in the correct order. There is a lip 42 on the collar section 39, which is aligned so that the lip fits under the lip of the tear-off band 22. As the collar section rotates clockwise the tear-off band 22 is torn off, so that after a complete revolution, 360°, the tear-off band 22 is completely removed. Simultaneously the safety mechanism is disengaged. This is illustrated by the cross-sections through the collar section shown in FIGS. 8*a* and *b*. In FIG. 8*a* the safety mechanism is engaged—that is the latch is in the safe position shown in FIG. 2*a*. On the inside of the collar section there is a pin 37 which extends into the device through the opening 28 in the upper sleeve 12 to impinge on the far side of the latch 6. The pin is in contact with the inner surface of the collar section. The inner surface of the ring section is a cam surface 43, so that as the collar rotates the action of the cam surface pushes the pin against the latch moving the latch from the safe position to the first position as shown in FIG. 8*b*. With the tear-off band 22 removed, the device can deliver as outlined above.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A device, comprising:

A needle-free injector comprised of an injection orifice;

a cap covering the injection orifice of the injector;

a mechanism for changing the injector from a safe position to a ready position to a triggering position;

wherein the cap is positioned such that the cap must be removed before the injector is placed in the ready position;

wherein the mechanism for changing the injector from the safe position to the ready position comprises a latch and wherein the device further comprises a mechanism for moving the latch from a latch safe position to a latch ready position, wherein the mechanism for moving the latch comprises a in and a means for actuating the pin, wherein, upon actuating the pin, the pin pushes the latch from the latch safe position to the latch ready position; and wherein the means for actuating the pin comprises a lever movable from a lever safe position to a lever ready position, and a collar at least partially encircling the injector, wherein actuating the lever moves the collar which moves the pin against the latch wherein the latch is moved from the latch safe position to the latch ready position.

2. The device as claimed in claim 1, wherein the mechanism for changing the injector from the safe position to a ready position to a triggering position further comprises:

an additional safety mechanism to prevent triggering of the injector;

wherein moving of the lever from the lever safe position to the lever ready position moves the collar; and wherein the additional safety mechanism is disengaged when the collar moves under the action of the lever moving from the lever safe position to the lever ready position.

3. The device as claimed in claim 2, wherein the additional safety mechanism is configured in a block shape to prevent triggering of the device by blocking the relative movement of components that cause the device to change from the ready position to the triggering position.

4. The device as claimed in claim 1, wherein moving of the lever exposes a button, wherein pressing of the button causes delivery of the injector contents.

5. The device as claimed in claim 1, wherein the lever is movable only after the cap is removed, wherein rotating the lever places the injector in the ready position.

6. The device of claim 1, an end of the lever is attached to the cap, and a base of the lever actuates a safety mechanism.

7. The device of claim 5, configured such that when the cap is removed, the end of the lever is exposed, allowing the lever to pivot pivoted, thereby placing the device in the ready position to deliver state.

8. The device as claimed in claim 1, wherein the mechanism for changing the injector from the safe position to the ready position further comprises:

an additional safety mechanism to prevent triggering of the injector wherein the additional safety mechanism is disengaged when the lever is actuated.

* * * * *

UNITED STATES PATENT AND TRADEMARK OFFICE
CERTIFICATE OF CORRECTION

| | | |
|---|---|---|
| PATENT NO. | : 7,776,007 B2 | Page 1 of 1 |
| APPLICATION NO. | : 10/596207 | |
| DATED | : August 17, 2010 | |
| INVENTOR(S) | : Jeffrey A. Schuster | |

It is certified that error appears in the above-identified patent and that said Letters Patent is hereby corrected as shown below:

Col. 8, at line 4, please replace "in" with --pin--;

Col. 8, at line 38, please insert the word --wherein-- after the "," and before the word "an";

Col. 8, at line 40, please replace "5" with --1--;

Col. 8, at line 42, please delete the word "pivoted";

Col. 8, at line 43, please delete the phrase "to deliver state".

Signed and Sealed this
Sixth Day of March, 2012

David J. Kappos
*Director of the United States Patent and Trademark Office*